United States Patent [19]

Wheeler

[11] Patent Number: 4,629,991
[45] Date of Patent: Dec. 16, 1986

[54] METHODS AND APPARATUS FOR DETECTING TUBULAR DEFECTS HAVING A PLURALITY OF EXPANDABLE ARCUATE SEGMENTS

[75] Inventor: Walter R. Wheeler, Friendswood, Tex.

[73] Assignee: PA Incorporated, Houston, Tex.

[21] Appl. No.: 599,197

[22] Filed: Apr. 11, 1984

[51] Int. Cl.[4] ............ G01N 27/72; G01R 33/12
[52] U.S. Cl. .................... 324/232; 324/242; 324/262
[58] Field of Search ............. 324/262, 226, 239–243, 324/225, 227

[56] References Cited

U.S. PATENT DOCUMENTS

| 2,467,306 | 4/1949 | Habig | 324/242 |
|---|---|---|---|
| 2,527,000 | 10/1950 | Drake | 324/218 |
| 2,882,488 | 4/1959 | Price et al. | 324/225 |
| 2,886,772 | 5/1959 | Gresham et al. | 324/241 |
| 3,103,976 | 9/1963 | de Vries et al. | 324/207 |
| 3,197,693 | 7/1965 | Libby | 324/225 |
| 3,237,446 | 3/1966 | Wood | 324/226 |
| 3,328,681 | 6/1967 | Wood | 324/225 |
| 3,337,796 | 8/1967 | Hentschel et al. | 324/233 |
| 3,343,079 | 9/1967 | Crouch | 324/227 |
| 3,379,970 | 4/1968 | Kusenberger et al. | 324/220 |
| 3,401,332 | 9/1968 | McClurg et al. | 324/227 |
| 3,529,236 | 9/1970 | Proctor | 324/220 |
| 3,538,433 | 11/1970 | Wood et al. | 324/232 |
| 3,555,412 | 1/1971 | Fowler | 324/228 |
| 3,560,845 | 2/1971 | Goldberg et al. | 324/243 |
| 3,579,099 | 5/1971 | Kanbayashi | 324/235 |
| 3,609,530 | 9/1971 | Johnson | 324/225 |
| 3,612,987 | 10/1971 | Placke et al. | 324/242 |
| 3,693,075 | 9/1972 | Forster | 324/220 |
| 3,835,374 | 9/1974 | Frost | 324/220 |
| 3,843,923 | 10/1974 | de Vries | 324/228 |
| 3,916,301 | 10/1975 | Vild et al. | 324/226 |
| 3,940,689 | 2/1976 | Johnson, Jr. | 324/221 |
| 4,061,967 | 12/1977 | Hall | 324/260 |
| 4,079,310 | 3/1978 | Osborne et al. | 324/226 |
| 4,096,437 | 6/1978 | Kitzinger et al. | 324/227 |
| 4,101,832 | 7/1978 | Baker et al. | 324/227 |
| 4,247,819 | 1/1981 | Shimanda et al. | 324/233 |
| 4,270,088 | 5/1981 | Weischedel | 324/241 |
| 4,292,588 | 9/1981 | Smith | 324/221 |
| 4,292,589 | 9/1981 | Bonner | 324/221 |
| 4,379,261 | 4/1983 | Lakin | 324/232 |
| 4,485,344 | 11/1984 | de Sivry et al. | 324/207 |
| 4,538,108 | 8/1985 | Huschelrath et al. | 324/232 |

FOREIGN PATENT DOCUMENTS 913780 12/1962 United Kingdom .

Primary Examiner—Ernest F. Karlsen
Assistant Examiner—Walter E. Snow
Attorney, Agent, or Firm—Norvell & Associates

[57] ABSTRACT

A tubing trip tool for use in determining the extent of defects in tubular sections of a continuous tubing string used in subterranean oil and gas wells is disclosed. The tubing trip tool is mounted on a surface rig surrounding the tubing string and defects are magnetically detected during tubing removal from the well bore. The tool comprises a segmented expandable detector head containing elements for measuring average wall thickness and local and axially extending defects. The expandable head is spring loaded and pneumatically actuated. Coupling detectors are located on the ends of the head to count tubing sections and to detect the presence of obstructions on the tubing to prevent damage to the detector head.

24 Claims, 13 Drawing Figures

METHODS AND APPARATUS FOR DETECTING TUBULAR DEFECTS HAVING A PLURALITY OF EXPANDABLE ARCUATE SEGMENTS

BACKGROUND OF THE INVENTION

1. FIELD OF THE INVENTION: This invention relates to defect inspection of tubular elements comprising a generally continuous tubular string used in a subterranean oil and gas well, and more particularly to inspection of tubular elements by detecting the properties of magnetic fields induced in the tubular elements during removal from the well.

2. DESCRIPTION OF THE PRIOR ART: Continuous tubular strings formed of connectable tubular sections or elements, such as production tubing strings, strings of drill pipe and casing strings, are used in the drilling, completion and production of subterranean oil and gas wells. The tubular elements comprising such strings are subject to mechanical damage while the tubular elements are located within the well and are also subject to the action of corrosive fluids which may be contained within the tubular elements or which may be transported through the tubular string between the well surface and a downhole location. It is therefore advantageous that the individual tubular elements comprising a tubular string be inspected periodically. Commonly, tubular elements or tubular sections are inspected for defects after the tubing string is removed from the well. Conventional inspection of tubular sections normally occurs after the individual tubing sections comprising the tubing string have been disengaged. Defect inspections are conventionally performed on a section by section basis. Occasionally, inspection is performed downhole through the use of inspection calipers. These tools leave "caliper tracks" and can be affected by the contents of the tubing.

A number of techniques exist for determining the presence of a defect in a tubing section. For example, the precise location of internal and external radially extending and three dimensional defects, including slug inclusions, mechanical damage, corrosion pitting and fatique cracks has been determined by flux leakage techniques in which a longitudinal magnetic field is induced by one or more magnetic induction coils. Surface riding detectors are located around the tubing and the maximum signal is recorded to precisely locate the defect. Since this magnetic inspection is conducted on a section by section basis after disengagement from the tubing string, when surface dirt, scale and mud can be controlled, detectors can be placed directly on the surface of the ferromagnetic tubular section to determine the presence of defects.

The location of longitudinal defects, including internal and external seams, plug scores, eccentricity, wear due to sucker rod interference, and wireline cuts, has been detected by inducing a circumferential magnetic field in the tubing. The field is induced by a high current discharge through an insulated rod on the interior of the tubing section. Detectors rotating around the surface of the tubing locate these longitudinal defects. Again, since the inspection is conducted on a section by section basis, the insulated rod can be inserted through the interior of the tubing section for this longitudinal defect inspection technique.

Other conventional inspection systems use methods which do not require insertion of rods and probes inside the pipe. Specifically, a common way of detecting longitudinal defects magnetically is the "rotating pole" method, where the magnetic field is applied from the outside by rotating electromagnets, and detectors positioned in between the poles scan the outside surface of the pipe.

Tubing wall thickness has been measured by measuring the radiation from a rotating radioactive source of gamma radiation transmitted through the wall of a tubing section. For example, with a source rotating around the pipe a detector may be located on the inside of the pipe to determine the degree of attenuation of gamma radiation and thus to determine the wall thickness. Again, this technique requires access to individual tubing sections after disengagement of the string. Other ways of measuring wall thickness with gamma radiation, which are backscatter, double-wall through-transmission and chord, have both the radiation detector and the source located on the outside of the pipe. Radiation methods introduce such problems as radiation licensing, record keeping, radiation safety administration, source handling complications, and fear of the unknown.

Techniques requiring surface-riding detectors, insertion of a detector or a driving means within the bore of tubular elements or requiring rotating mechanical means to obtain a complete circumferential coverage of tubing sections are unsuited for use is defect inspection and measurement of tubing sections while the string is being removed from the well. These defect inspection techniques are also unsuited to the measurement of defects in tubing sections while the sections are interconnected in the tubing string. Thus these inspection techniques are not suitable for use on a drilling, completion or workover rig at the surface of the well to measure defects in a tubing string as the string is removed from the well. In addition to the requirements that only disengaged tubing sections be individually measured, additional problems which would be encountered are the limited space available on the rig, the inability to control the longitudinal velocity of the tubing string as it is removed from the well, and the difficulty in precisely controlling the transverse location of the tubing sections comprising the tubing string. Furthermore, the use of surface detectors in a tubing trip tool for measuring defects as tubing sections, comprising a tubing string, are removed from the well is also complicated by the presence of solid deposits, such as drilling mud, and tubing mounted components, such as retrievable packers, which may be incorporated into the tubing string. One technique for inspecting tubular elements which is adaptable to relative movement, at variable velocities, is a technique involving the use of a saturating longitudinal magnetic field and the subsequent measurement of the time integral of the electrical signal caused by the magnetic field applied to the ferromagnetic tubular member to determine the average wall thickness. Testing using this technique has been conducted for surface pipe installations in which the magnetic field and the flux detecting elements are moved relative to a continuous pipe array. Such apparatus has not, however, been employed to measure the average wall thickness of tubing sections as they are removed from an oil or gas well.

SUMMARY OF THE INVENTION

An expandable tubing trip tool for use on a subterranean well rig has a segmented detector head radially shiftable from an inner measuring position to an outer retracted position. Coils for inducing longitudinal and transverse magnetic fields are included in the tubing trip tool. Detector elements, comprising coils and Hall effect probes, are contained in the expandable detector head. These elements detect changes in magnetic field induced in the tubular elements, and the average wall thickness, local defects, such as corrosion pitting, axial defects, such as sucker rod interference wear, and tubing velocity are measured.

The detector head is transversely spaced from the tubing even in the inner measuring position so that deposits on the exterior of the moving tubing do not interfere with the detecting head. Coupling or obstruction detectors are located on the ends of the tool to count tubing sections for subsequent identification of the defect location and to provide a warning of an approaching obstruction, such as a packer or other downhole tool.

The radially shiftable detection head segments are biased to the retracted position and are pneumatically shifted to the inner measuring position. In the preferred embodiment of the invention, an inflatable toroidal ring or hose is disposed aroung the expandable detection head segments. Inflation of the hose shifts the segments to the inner measuring position. A valve is provided to deflate the hose when the segments are to be retracted. Centering blocks engaging the tubing are also provided to maintain a cage containing the detector head segments generally centered relative to the transversely shiftable tubing during axial movement of the tubing.

DESCRIPTION OF THE PREFERRED EMBODIMENT

Tubing Trip Tool

Figure 1:
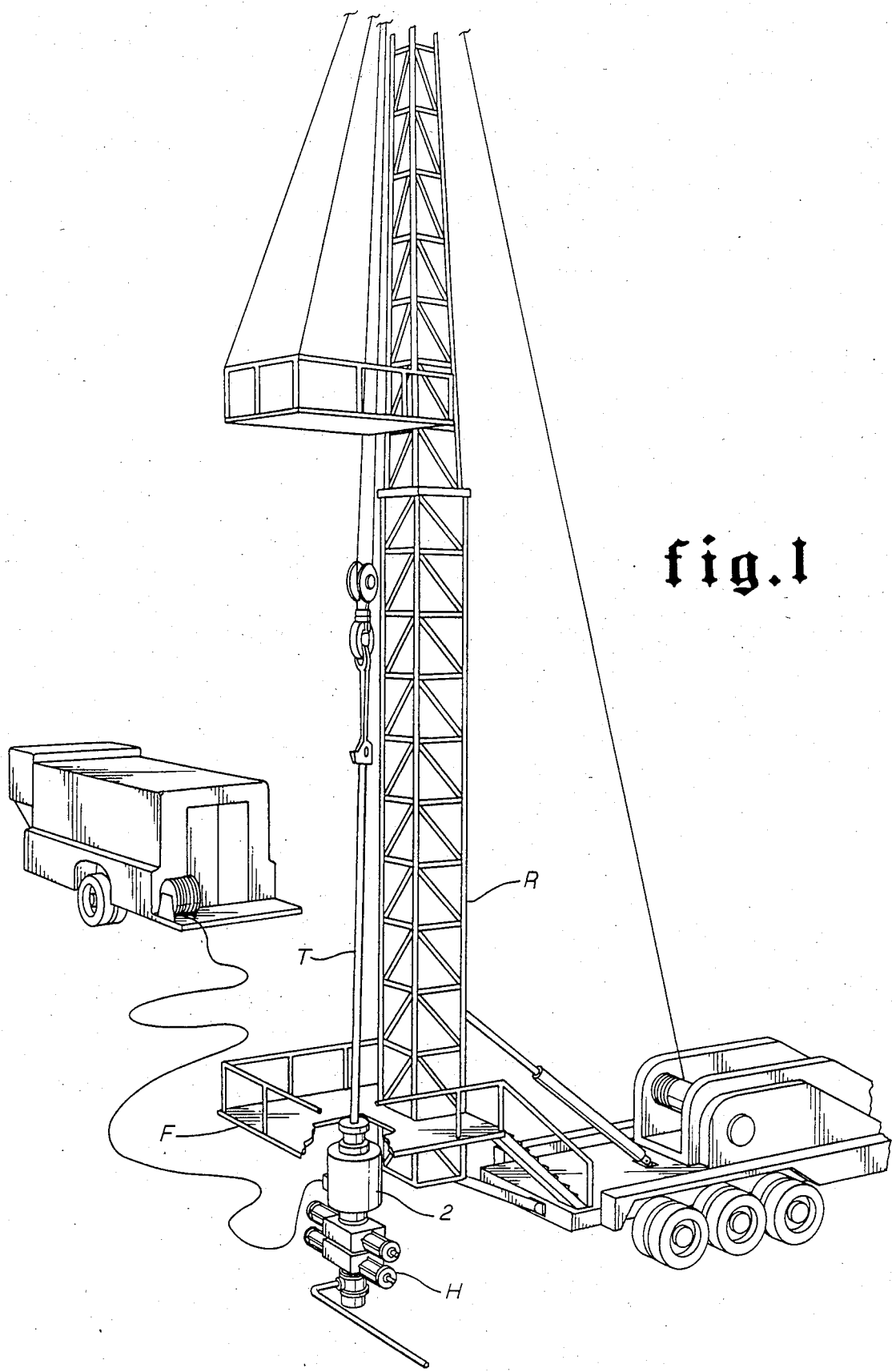
FIG. 1 is a schematic showing the tubing trip tool on a surface well rig.

A conventional workover rig illustrated schematically by rig R in FIG. 1, having a superstructure for hoisting and lowering, is used to remove a tubular string, such as a casing, drilling or tubing string represented by tubing string T, from an oil or gas well during workover or servicing operations. Workover operations normally involve the removal of the tubular string to permit operations intended to restore or increase production in a producing well. Typically the original tubing string is reused if the respective tubular elements are in satisfactory condition. FIG. 1 illustrates the use of a tubing trip tool 2 at the rig site to measure defects in each tubular element as it is removed from the well. A tubing trip tool 2 comprising the preferred embodiment of this invention can be positioned on the wellhead below the horizontal rig floor F so as not to interfere with conventional operations on the rig. The tubing trip tool can be attached directly to the blow out preventers on the well.

Figure 2:
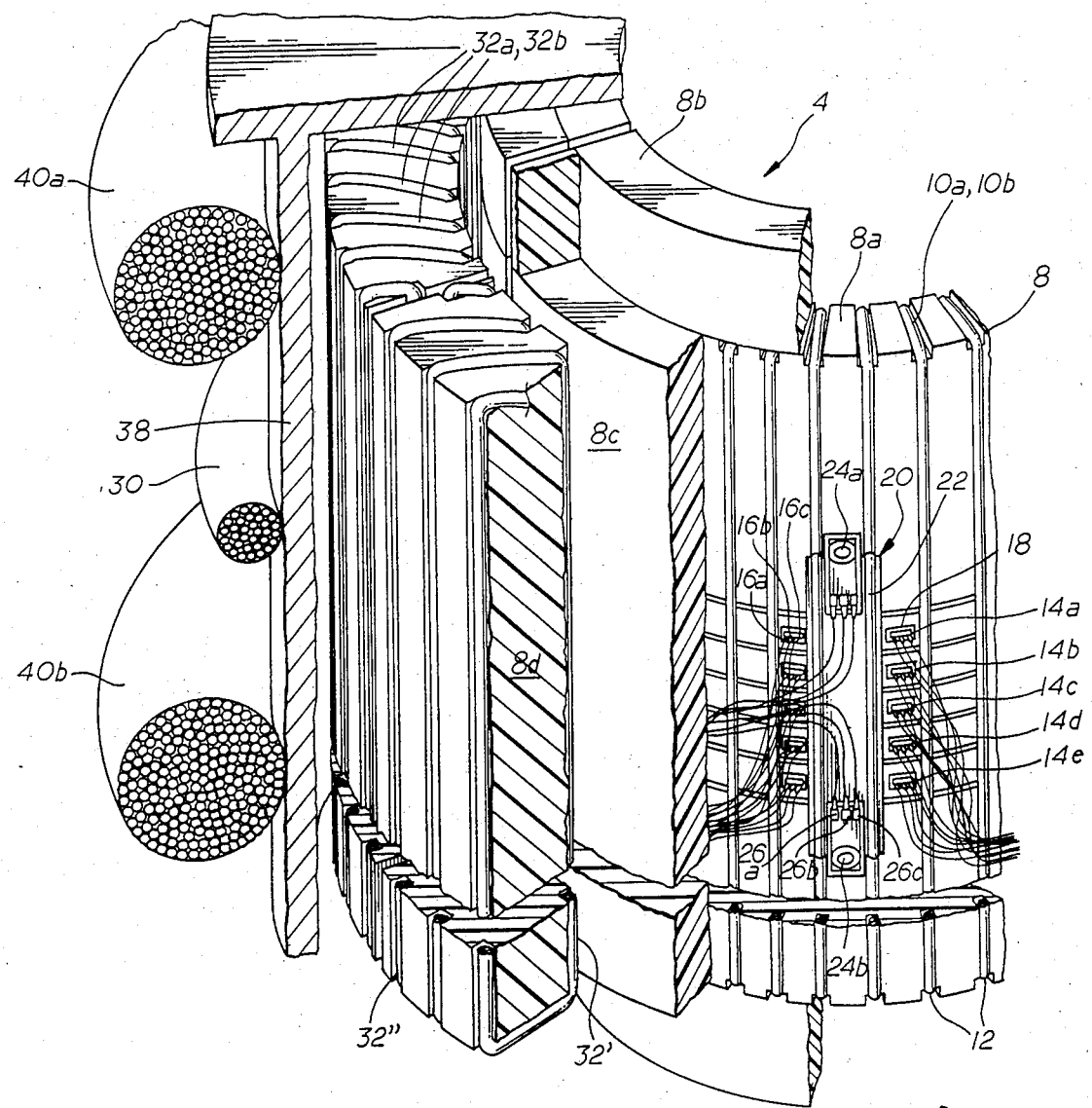
FIG. 2 is a view of a segment of the tubing trip tool in the expanded configuration.
Figure 3:
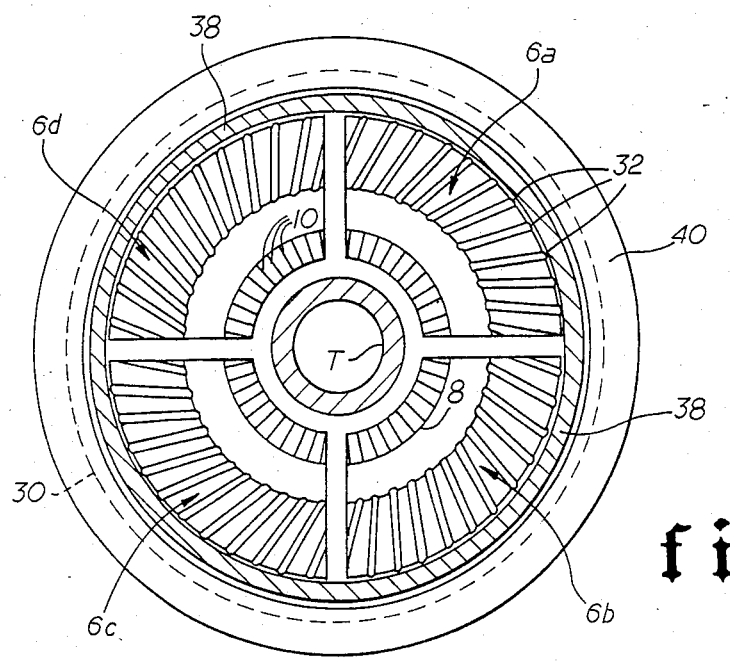
FIG. 3 is a cross-sectional view of the tubing trip tool head in the expanded configuration.
Figure 4:
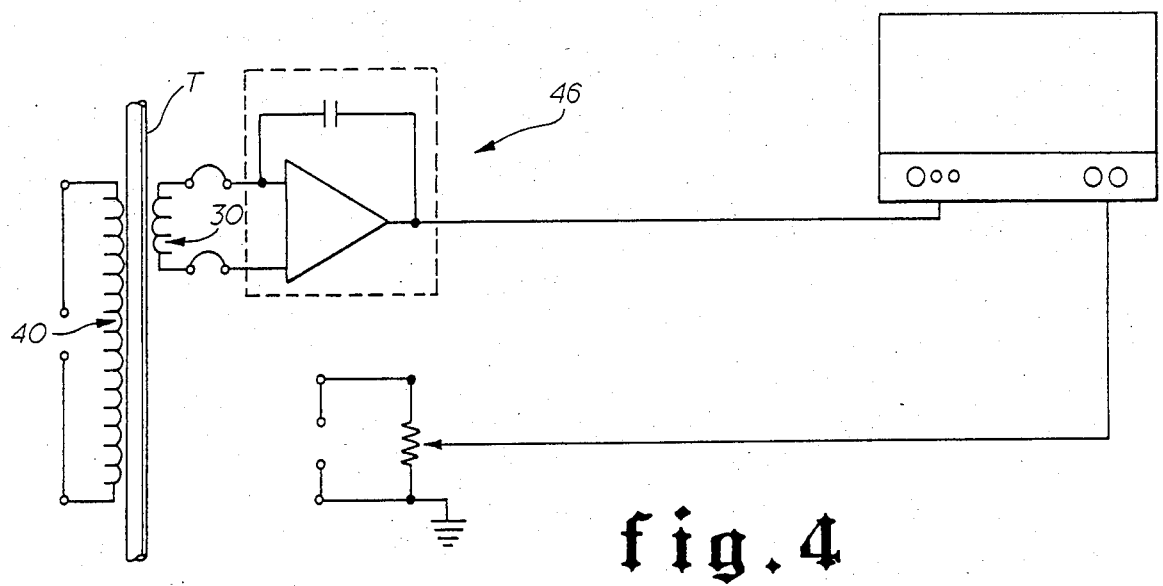
FIG. 4 is a schematic of the wall thickness measurement circuitry.
Figure 5:
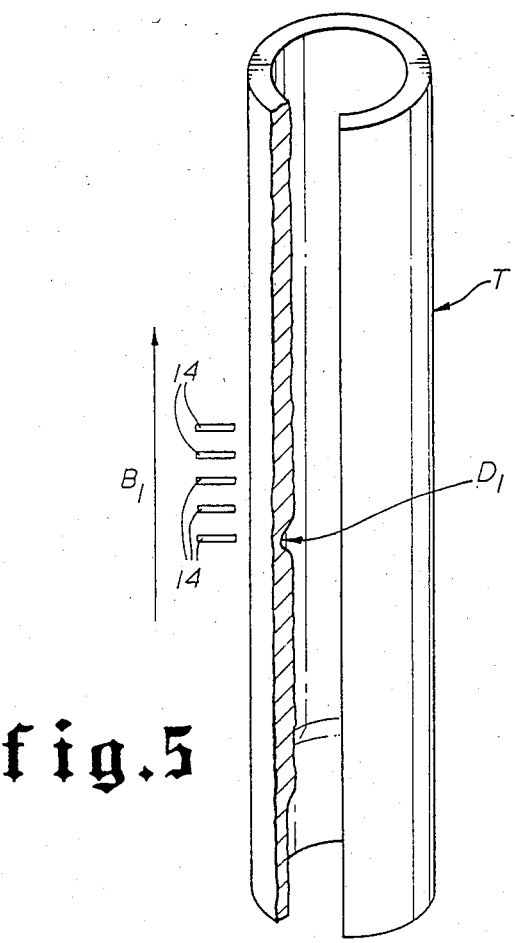
FIG. 5 is a view showing the tubing string and the detectors for measuring local defects.
Figure 6:
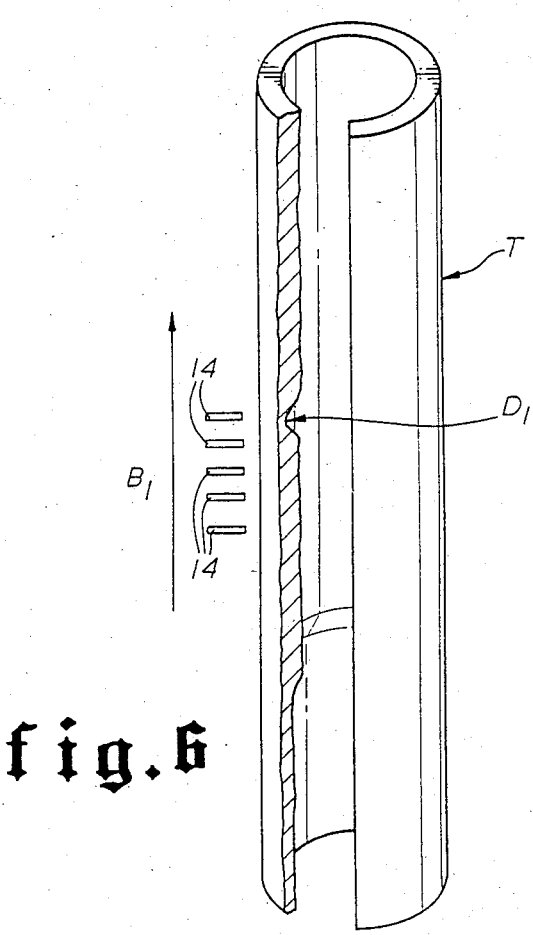
FIG. 6 is a view similar to FIG. 5 showing relative movement of the tubing.
Figure 7:
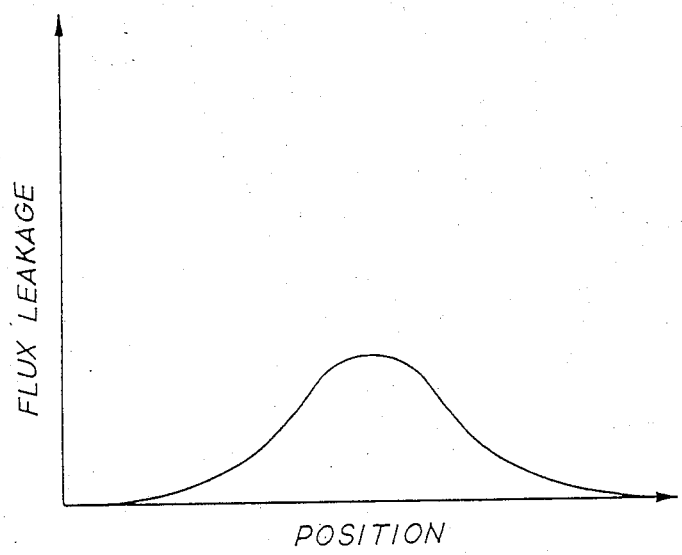
FIG. 7 shows the effect of movement of the tubular element upon flux leakage.
Figure 8:
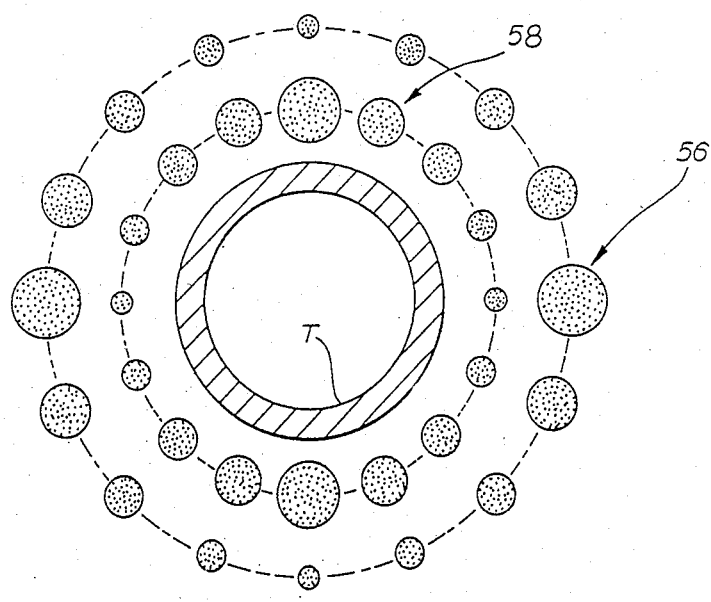
FIG. 8 is a cross-sectional schematic showing the sinusoidal orientation of sine and cosine coils relative to the tubular element.

A segment of the tubing trip tool head 4 is shown in FIG. 2. The head includes two separate driving coils, two separate detecting coils, and a plurality of discrete detecting elements to determine the extent of defects in the tubing sections. A velocity detector for determining relative velocity between the head and tubing sections is also included. The preferred embodiment of this invention comprises an expandable head having four segments 6a-6d as seen in FIG. 3. Each segment is an encasement 8 which comprises multiple components. The encasement 8 is fabricated from a material that has the properties of an electrical insulator. In the preferred embodiment of this invention, encasement 8 can be formed from an encapsulation material or potting compound which will insure that the proper amount of space is maintained between the electrical components. The encapsulation material will occupy any spaces or voids surrounding the components, and will provide a barrier between the electrical components and the atmosphere surrounding encasement 8, thereby rendering encasement 8 safe for use on the wellhead where explosive vapors can be encountered.

Two separate AC detecting coils 10a and 10b are carried on the innermost insulating body section 8a. The circumferentially continuous coils 10a and 10b are wound in appropriate grooves on body section 8a and a plurality of separate loops are formed around body 8a. These separate loops, each of which contains conductors forming the separate detecting coils 10a and 10b, are positioned in a radial plane on encapsulating member 8a. Each loop is generally defined by two radially spaced, axially extending coil conductor sections and two axially spaced, radially extending coil conductor sections. The coil conductors then define an annular volume encircling the tubular sections passing axially therethrough. Radially extending planes between the coil conductors will be generally perpendicular to magnetic field lines detected by coils 10a and 10b as will be subsequently more completely discussed.

A plurality of flux leakage detecting elements 14a-14e are also located in the inner encapsulating body section 8a. In the preferred embodiment of this invention, each of the flux leakage detecting probes 14a-14e comprises a separate probe in which voltage is generated in response to the Hall effect. The plane of each Hall probe is perpendicular to the axis of the tubing trip tool head 4 and is located perpendicular to each tubular element moving axially relative to the tubing trip tool head 4. In the preferred embodiment of this invention, separate groupings of five Hall effect flux leakage detecting probes are positioned at different angular positions around the tubing trip tool head 4. Each of the Hall probes 14a-14e is received within corresponding slots 18 extending into the insulating body section 8a. In the preferred embodiment of this invention, five equally spaced probes are positioned at each angular location.

One or more velocity detectors 20 is positioned on the exterior of insulating body section 8a. In the preferred embodiment of this invention, each velocity detector 20 comprises a detector circuit or coil 22 having two or more Hall probes 24a and 24b located within the circuit. The plane of the velocity detector circuit or coil 22 is perpendicular to a radial plane extending through the tubing trip tool head 8. The plane of the individual Hall probes 24a and 24b in the velocity detector is perpendicular to the plane of the Hall probe 14a-14e used for flux leakage detection.

The AC magnetic detecting coils 10a and 10b, the flux leakage detecting probes 14a-14e and the velocity detector 20 are each radially spaced from the tubing element T in which defects are to be measured. In the segmented embodiment of the invention shown in FIG. 2, the individual segments can be shifted radially from a measuring position to an outer position to permit obstructions to move past the tubing trip tool head. Each of the detector coils is, however, spaced from the surface of the tubing T in the inner measuring position. In the preferred embodiment of this invention, the inner surface of the tubing trip tool head 4 is positioned approximately two-thirds of an inch from the surface of the tubing element T.

Insulated body sections 8b and 8c surround the detecting coils and probes mounted on insulating body section 8a. Epoxy or some other potting material can also be used to insure that all potential electrical leakage paths are appropriately isolated from each other and from the atmosphere.

Outer AC driving coils 32a and 32b are positioned around insulating body section 8d. The AC drive coils 32a and 32b each comprise continuous coils having an angular conductor distribution similar to that of AC detecting coils 10a and 10b. The sinusoidal distribution in the coils 32a and 32b is relatively offset so that the connector distribution phase differs between drive coils 32a and 32b. In the preferred embodiment of this invention, the conductor distribution is offset by 90° so that coil 32a can be referred to as a sine coil and coil 32b can be referred to as a cosine coil. Coils 32a and 32b each completely encircle the tubing trip tool head 4 and tubular element T with separate loops, containing conductors from each coil 32a and 32b, being formed in radial planes around the tubing trip tool head 4. On the exterior, AC driving coils 32 are encapsulated within the common encapsulating insulating body 8 of the tubing trip tool 2.

In the preferred embodiment of this invention, an outer metal sheath 38 as illustrated in FIG. 2, can be positioned around the exterior tubing trip tool head. This outer metal sheath, which corresponds to housing 60 in FIG. 12, can be fabricated from a material, such as aluminum or stainless steel, serves as a carrier for the outer DC drive coils 40a and 40b in FIG. 12. In the preferred embodiment of this invention, the DC drive coils can be separated into two separate bundles. A single drive coil bundle can also be used. The encircling drive coils 40 contain a sufficient number of amp turns to saturate the tubular element T passing through the tubing trip tool. Encircling coil 30 extends completely around the circumference of the tubing trip tool head 4 and surrounds the tubular element T at a greater radial spacing than the detecting elements 10a and 10b, 14a-14e, and 20.

Expandable Head

Figure 12:
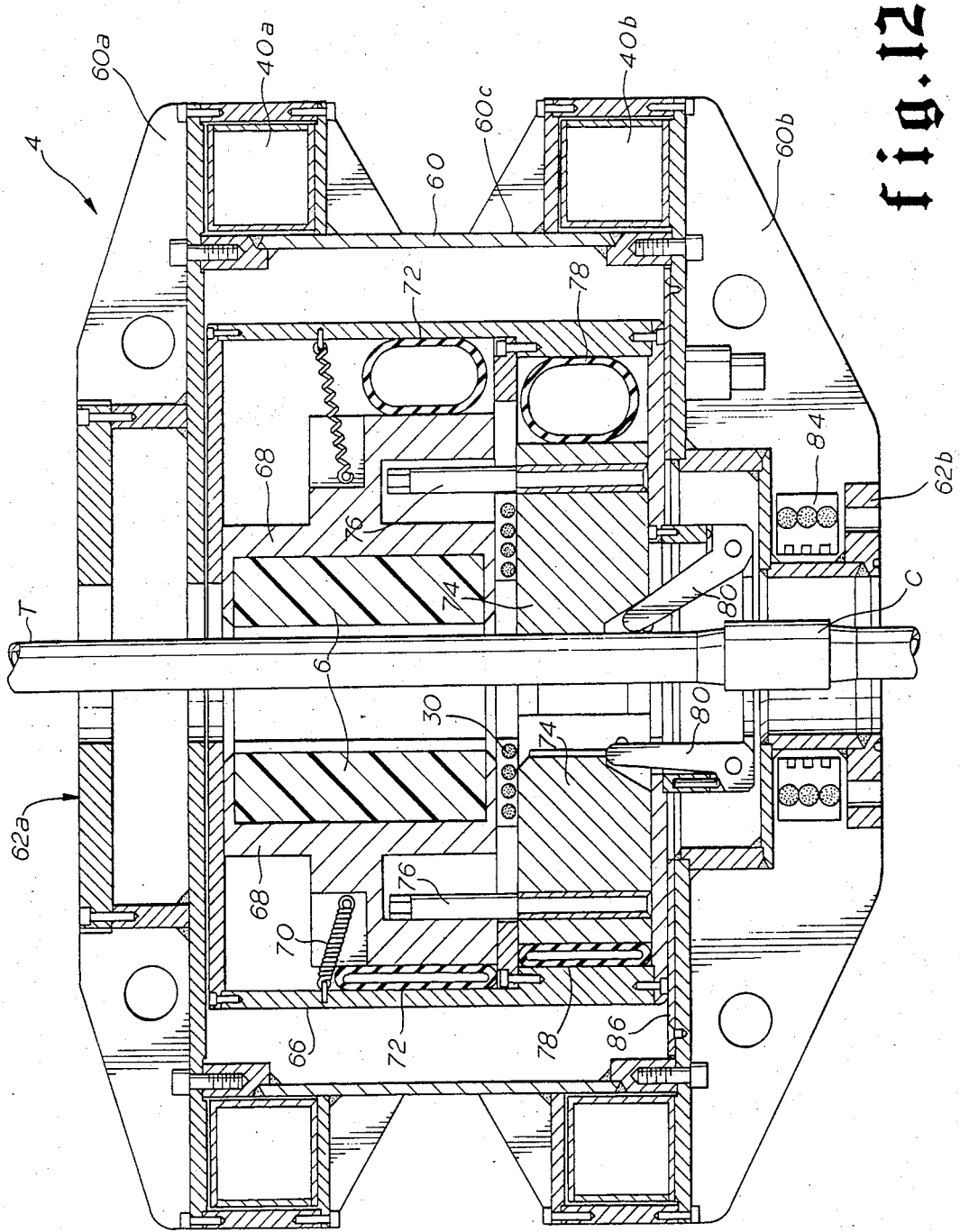
FIG. 12 is a view of the expandable tubing trip tool head showing the inner measuring position and the outer retracted position.

FIG. 12 is a vertical sectional view of one version of an expandable tubing trip tool 4. The expandable head shown therein can be positioned below the rig floor and provides central clearance for oil field tubing T or any object passing through up to well bore size. FIG. 12 illustrates the expandable head comprising the preferred embodiment of this invention in two different positions. The portion of the tool to the right of the tubing T in FIG. 12 depicts the tool in its innermost measuring position. The portion of the tool located to the left of the tubing T in FIG. 12 depicts the tool with the detecting elements shifted to an outermost position to provide clearance for obstructions in the tubing string up to well bore size, such as packers or tubing anchors. It should be understood that both the right and left portions of the tool comprising the preferred embodiment of this invention are radially shiftable in unison, and separate elements of the tool do not occupy the separate positions shown in FIG. 12. Two opposite elements of the tool are merely shown in the configuration of FIG. 12 for the purposes of explaining and comparing the open and closed modes of operation of the tool.

An outer cylindrical housing 60 comprising upper and lower sections 60a and 60b and cylindrical section 60c provides mounting plate for slips 62a and flange 62b for mounting the expandable head on the blowout preventers. It should be understood that the expandable head shown in FIG. 12 is comprised of a plurality of radial segments, each of which is adapted to shift inwardly and outwardly in unison with the other segments. FIG. 2 discloses a four segment expandable head containing the same essential elements as FIG. 12. A central opening provides clearance through the tool for passage of the tubing and any obstructions carried therethrough. A floating detector cage 66 is positioned on the interior of outer tool housing 60. Floating detector cage 66 is not fixed to the outer housing 60 and is free to move radially in response to radial motion of the tubing. In the preferred embodiment, the lower surface of cage 66 rests on a low friction sliding surface 86 which is mounted on the lower portion 60b of the outer tool housing.

A plurality of arcuately shaped detector mounting blocks 68 are positioned within the upper portion of the detector cage 66. Each of the detector mounting blocks contains an arcuate detector segment corresponding to one of the segments 6a-6d shown in FIG. 2 which, in the preferred embodiment, includes the transverse magnetic field detecting elements 10, the flux leakage detecting elements 14, and the velocity detecting elements 20. The construction of the elements in the detector housing of the embodiment of FIG. 12 is shown in greater detail in FIG. 2 and FIG. 3.

Each detector mounting block 68 is attached to the detector cage 66 by means of a coil spring 70 which biases the detector block 68 outwardly relative to the centrally disposed tubing. A continuous inflatable detector air bag 72 displaces each mounting block 68 to the innermost position to locate the detector head in the inner measuring position as shown in the right hand portion of FIG. 12. Air bag 72 is connected to an appropriate source of compressed air. A fast acting valve of conventional construction can also be positioned in communication with air bag 72 so that outward movement of connector blocks 68, tending to deflate the air bag, can be accomplished by venting the air within the air bag through the conventional valve.

Centering blocks 74 are located below the detector blocks 68. These centering blocks 74 comprise arcuately shaped mounting members which, in the innermost position as shown in the right hand side of the figure, engage the exterior of the tubing T to center the detector elements with respect to the tubing. Note that in the preferred embodiment of this invention, the centering blocks are in engagement with the tubing T but the detecting elements 6 mounted in blocks 68 are spaced slightly from the periphery of the tubing T when in an inner measuring position as shown in the right hand portion of FIG. 12. In the preferred embodiment of this invention, the spacing between the periphery of the tubing element and the detector element is approximately two-thirds of one inch. As shown in the left hand portion of FIG. 12, the centering blocks 74 are radially shiftable to open up to well bore size and provide clearance so that obstructions affixed to the tubing, such as packers, tubing anchors, etc. can move therethrough. In the normal operating mode, each coupling passing through will force the centering blocks radially outward while maintaining centering with respect to the tubing, but without radially displacing the head.

Each centering block 74 has an upstanding pin 76 received within a companion slot within the mounting block 68. Movement of the centering block away from the tubing string to an extent greater than required to pass a coupling brings the corresponding pin 76 into engagement with the detector mounting block 68, as shown in the left hand portion of this figure, to move detector elements 6 radially outward. Centering blocks 74 are also biased radially outward by springs (not shown) and are displaced inward by air bag 78. In the preferred embodiment of this invention, air bag 78 acts in virtually identical fashion to air bag 72, although air bags 72 and 78 are separate structures. Each communicates with a source of compressed air but neither air bag communicates directly with the other air bag.

In addition to the centering blocks 74, four equally spaced fingers 80 located at the lower portion of the expandable head are also positioned to contact the tubing T. Fingers 80 also engage a mating inclined surface on centering block 74. When an unexpected obstruction on tubing T engages finger 80, the fingers will act to push the centering block 74 radially outward thus moving detector mounting blocks 68 out of the way to prevent damage during passage of the obstruction. The passing through of a coupling, however, will not effect radial movement of the detector mounting blocks. Outward movement of the centering blocks 74 and detector mounting blocks 68 can also be provided by a command signal when movement of an obstruction, larger than coupling C, such as a packer or other well tool, is anticipated. In other words, the detecting elements are selectively expandable only upon movement of an obstruction or component of the tubing string larger than a coupling. Such movement will occur by deflating air bags 72 and 78 on signal to permit springs 70 to shift the mounting block and the centering blocks outwardly to clear the obstruc- tion.

An automatically triggered signal indicating that an obstruction larger than a coupling is present may also be obtained from coupling detectors 84 mounted on lower mounting housing section 60b. These coupling detectors can comprise a DC drive coil having sufficient amp turns to saturate the tubing adjacent thereto with encircling detector coils for determining changes in the total magnetic flux to indicate that an obstruction substantially larger than a coupling is approaching the expandable detector head.

In addition to the detector element segments 6 located in detector mounting blocks 68, the expandable head shown in FIG. 12 also includes both DC and AC drive coils. The AC drive coils used in the expandable head are positioned in the detector head element segments 6. The construction of the AC drive coils used in such expandable heads correspond generally to the configuration of the AC drive coils 32 shown in FIG. 2. DC drive coils containing a sufficient number of amp turns to saturate the tubing T are mounted on the exterior or interior of the expandable head. These drive coils 40a and 40b are positioned such that a uniform longitudinal saturated magnetic field can be induced in the tubing T in the vicinity of the detector head segments 6. The expandable head depicted herein can also be constructed utilizing a single DC drive coil 40.

Wall Thickness Measurement

The tubing trip tool 2 measures the wall thickness of a tubing section by using a technique in which the total flux induced in the tubing section by a saturating magnetic field is measured. The ferromagnetic tubing section within the saturating magnetic field is saturated when the magnitude of the magnetic field induced in the ferromagnetic element is at a maximum and does not increase as a result of a further increase in the saturating magnetizing field. Thus the saturating magnetizing field can produce a uniform saturated magnetic field in a tubing section having a specified cross-sectional area. In other words, the total magnetic flux is dependent upon the cross-sectional area or wall thickness of the tubular section. If the saturating magnetizing field is uniform, the contribution of the total flux induced by the magnetization of the pipe material within a given area varies as the cross-sectional area of the tubing section. By providing a large number of amp turns in a coil 40 encircling a tubing section, a saturated magnetic field extending longitudinally within the wall of the tubing section can be produced.

The total flux through an area intersecting the axis of the tubing section and intersecting the longitudinal saturated magnetic field can be measured by pickup coil 30 encircling the tubular section. The area of the pickup coil would preferably, but not necessarily, be perpendicular to the axis of the tubing section. The total flux through the pickup coil can be detected by signal integration. The EMF induced in a pickup coil is directly related to the time rate of change of the flux through the coil. Thus the total flux can be detected by integrating the EMF produced in the coil over time. In fact, a virtually linear dependence of the total flux through the pickup coil with average wall thickness can be obtained. Thus a convenient direct measurement of average wall thickness can be made.

In the tubing trip tool 2, the saturating magnetizing field is applied by one or more DC drive coils 40. In the preferred embodiment of this invention, two drive coils 40a and 40b are positioned on the exterior of the tubing trip tool head 4 (see FIGS. 2 and 12). The pickup coil 30 encircling the tubular section T detects the total flux, and the output of pickup coil 30 can be attached to a conventional integrator 46. The output voltage of the integrator is a direct measure of tubing wall thickness. If the tubing moves axially relative to the stationary saturating magnetizing field, a continuous measurement of total flux will result in a measurement of the wall thickness along the length of the tubing section. Conventional signal processing means can be used for comparing and correlating detected signals with average wall thickness.

This noncontact measurement of average wall thickness can be incorporated into the tubing trip tool 2 comprising the preferred embodiment of this invention. A sufficiently strong and uniform DC magnetizing field can be produced by a sufficient number of amp turns in coils 40a and 40b. For example, approximately 5,000 amp turns can saturate a 2⅜″ OD pipe, a standard size tubing section used in an oil and gas well. In the preferred embodiment of this invention, a sufficient uniform longitudinal saturated magnetic field is produced in a tubing section moving relative to the saturating magnetic field within a range of velocities normally encountered in the removal of a tubing string from an oil or gas well. A coil having an overall height of less than one foot has been found to satisfactorily produce a longitudinal saturated DC magnetic field in the tubing section and an accurate measurement can be obtained of the average wall thickness.

Local Defect Detection

The average wall thickness of a ferromagnetic tubular member or pipe can be determined by detecting the total flux induced by the saturating magnetizing field within the element. Qualitative information as to the changes in surface texture due to such factors as internal and external corrosion, can be determined by comparing average wall thickness at different locations on the tubular member. The difference between the signals produced in separate coils will not yield quantitative information as to the state of local defects in the tubular members.

In tubular sections used in oil and gas wells, corrosion on the tubular member can result in localized corrosion pits $D_1$ which can seriously reduce the strength of individual tubing sections. Since the thickness of the remaining wall of the tubular sections determines the ability of individual tubular sections to function in the work environment, the depth of local corrosion pits must be quantified to determine the acceptability of the tubular sections.

It is common practice to grade used tubing based upon the depth of corrosion pits. Although each separate corrosion pit would contitute a local defect $D_1$, the dimensions of which would generally be less than the diameter of the tubular element, the nature of the corrosion phenomenon would result in a plurality of irregular and overlapping corrosion pits being located in the same general region on the interior of a tubular section. Of course the flux leakage will be dependent upon the overall size of the individual corrosion pits and not just the depth of the corrosion pits. Thus the length and width of the corrosion pits would affect the flux leakage detected. Other factors, such as the contour or shape of the corrosion pits and the extent of any discontinuities in the shape of corrosion pits, would also affect the flux leakage. Thus the leakage fields of different pits having the same depth in a tubular section will differ for different lengths and widths of the pits as well as for a different contour of the pits. Background field or noise due to unrelated phenomenon can also affect the signal corresponding to flux leakage and the saturated magnetic field within the pipe.

In the preferred embodiment of this invention, a plurality of flux leakage detecting elements 14 are disposed within the saturating magnetizing field. These flux leakage detecting elements are disposed at a plurality of axially spaced positions within the saturating magnetizing field. In the preferred embodiment of this invention, a plurality of discrete probes having an output produced by the Hall effect are used. In the preferred embodiment of this invention, identical flux leakage detecting Hall probes 14a-14e are equally spaced at five separate axial positions. Although only two sets of flux leakage detecting Hall probes 14a-14e are shown in FIG. 2, it should be understood that corresponding sets of multiple elements are circumferentially disposed around the tubing trip tool head to provide complete coverage around the periphery of the tubular element to detect local defects, such as corrosion pits located at different angular positions.

In the preferred embodiment of this invention, the individual flux leakage detecting Hall probes are oriented such that the plane of the Hall sensing element is perpendicular to the axis of the moving tubular element. Hall elements, such as the type used herein, produce an output voltage proportional to the product of the input current, the magnetic flux density, and the sine of the angle between the magnetic flux density and the plane of the Hall generator. Thus a maximum voltage output from a given leakage field would be produced by orienting the individual flux leakage detecting Hall probes perpendicular to the saturated magnatic field. The DC drive coils 40a and 40b are positioned to induce a longitudinal or axial saturated magnetic field within the tubular element T. By orienting the probes 14a-14e perpendicular to the longitudinal saturated magnetic field within the pipe, the flux leakage detecting probes are situated to detect longitudinal changes in the magnetic field. Of course transverse magnetic field changes would also occur as a result in the change in the longitudinal saturated field within the tubular member. Orientation of flux leakage detecting Hall probes perpendicular to the radius of a moving tubular section would be ideal to detect these transverse field changes. However, it is understood by those skilled in the art that the transverse magnetic field changes are related to longitudinal magnetic field changes. Thus a plurality of individual flux leakage detecting Hall probes oriented at right angles to the probes 14a-14e used in the preferred embodiment of this invention could also be used. Of course flux leakage detecting elements other than Hall probes can also be employed in the measurement of localized defects, such as the depth of corrosion pits. For example, the change in flux linking a coil will also result in a signal which can be employed for local defect measurement. However, the output signal from a coil must be integrated to obtain the same output independent of the velocity of the tubing element T, as would be obtained with a Hall probe.

It has been found that the magnitude of the flux leakage detected by elements 14 does not provide an adequate quantitative measure of the depth of local defects, such corrosion pitting defects, on a tubular element. The fact that flux leakage is dependent upon the size and shape of localized defects, such as corrosion pitting, rather than upon the depth alone, is believed to account for the inability to measure localized defect depth by measuring flux leakage magnitude alone. However, it has been found if effects due to the length and width of defects, such as corrosion pitting, can be removed, the resulting signal results in an accurate measurement of the depth of the local defect.

In the preferred embodiment of this invention, a signal corresponding to the depth of local defects, such as defects due to corrosion pitting, can be determined by differentiation of the magnitude of the flux leakage relative to the axial or longitudinal dimension of the moving tubular member.

Axial Defect Measurement

The bore of a tubular member of tubing section T used in a tubular string in a subterranean oil and gas well can often have axially extending defects $D_2$ located at one or more circumferential positions on the tubing. An example of axially extending defects are defects due to sucker rod wear. Sucker rod wear on the bore of the tubing occurs when the sucker rod contacts the tubing during reciprocal movement of the sucker rod. However, sucker rod interference is not uniform around the circumference of the bore of the tubing section or tubular element. Sucker rod wear often occurs at only one circumferential location, although it is not uncommon for a sucker rod to oscillate laterally causing sucker rod interference at two opposite points. The loads placed on the individual sucker rod assembly will normally result in continual interference between the sucker rod and the tubing at the same locations.

Since the length of the sucker rod stroke is normally large compared to the diameter of the tubing, the length of the sucker rod defects can be expected to be greater than the diameter of the tubing. Although sucker rod wear is a common occurrence, points at which the sucker rod interferes with the bore of a tubing string may occur in only a fraction of the tubing sections if the distance between interfering sucker rod nodes is greater than the length of individual tubing sections. Not only must the tubing sections subjected to sucker rod wear be identified, but the depth of axial defects, such as sucker rod wear defects, must also be measured. The depth of the defects due to sucker rod wear is significant because the reduction in the strength of the individual tubing section increases with the depth of the axially extending sucker rod wear defect.

Axial defects $D_2$, such as defects due to sucker rod interference, can be detected by employing a fluctuating AC magnetizing field $B_2$ in addition to a uniform DC magnetizing field $B_1$. Even if a uniform DC magnetizing field in the longitudinal or axial direction is of sufficient intensity to saturate the ferromagnetic element or tubular section within the DC field, as is the case with the field used to determine wall thickness, the addition of a fluctuating AC transverse magnetic field will result in detectable changes in the magnetic state of the ferromagnetic element located within both fields. In fact, the DC field enhances the penetration of the AC field in the tubular sections. Of course the detectable changes resulting from the addition of the fluctuating transverse field will be dependent upon the geometry of the tubular element. For example, the response of an undamaged tubing section would differ from the response of a similar tubing section containing an axially extending defect, such as a rod wear interference defect. In the preferred embodiment of this invention, the changes due to such axially extending defects as sucker rod interference defects $D_2$ in an oil field tubular section can be detected even where the strength of the fluctuating transverse magnetic field is significantly less than the strength of a uniform saturating DC magnetizing field. It has been found that measurement of axial defects, such as sucker rod interference defects, can be made by applying a sinusoidal transverse magnetizing field having a frequency of approximately 100 Hz. and an intensity of approximately 1/10th the intensity of a uniform saturating magnetizing field applied in the longitudinal direction. In the preferred embodiment of this invention, drive coils 32 are used to apply such a fluctuating magnetizing field.

Although the response due to the application of a transverse fluctuating magnetic field in addition to the uniform longitudinal saturating magnetic field will in part be due to flux leakage effects, the principal response will be due to eddy current effects. In order to obtain full circumferential coverage of a tubular section and to obtain a measurable response, the preferred embodiment of this invention comprises an apparatus and method for rotating the fluctuating AC magnetizing field around the tubular section T as the tubing section moves axially relative to both the AC magnetizing field $B_2$ and the uniform DC saturating magnetizing field $B_1$. Thus the rod wear defect response measured in the preferred embodiment of this invention is due to an AC magnetizing field rotating around the tubing section and having a constant magnitude.

Figure 9:
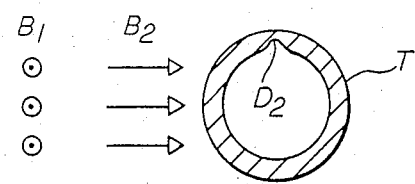
FIGS. 9-11 illustrate the rotation of the fluctuating magnetic field around a tubular element to detect axially extending defects at different angular positions relative to the driving magnetic field.
Figure 10:
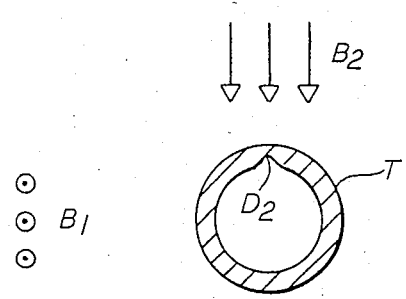
Figure 11:
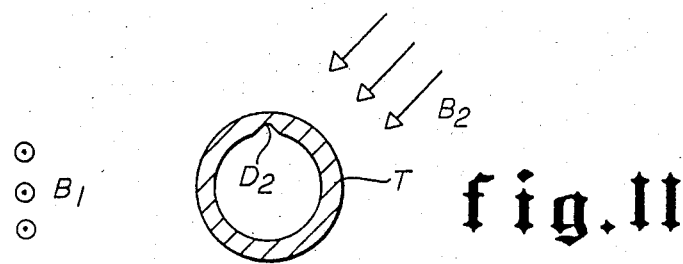

The rod wear detecting apparatus employed in tubing trip tool head 4 in the preferred embodiment of this invention can detect and measure rod wear defects $D_2$ at arbitrary circumferential positions in a tubing section or tubular element which may be moving axially at different and nonuniform velocities. When used in a tool for detecting rod wear defects as a tubing string is removed from an oil and gas well, the velocity of the tubing sections can be up to 300 feet per minute. Rotation of the magnetic field around the moving tubular sections to obtain complete circumferential coverage of the tubing sections cannot be practically accomplished by mechanically rotating the apparatus inducing the transverse fluctuating magnetizing field. In the preferred embodiment of this invention, rotation of the magnetic field is accomplished by employing separate phase windings in the drive coils 32 which generate the fluctuating transverse field. Thus the field is rotated electrically rather than mechanically. In the preferred embodiment of this invention, the drive coils 32a and 32b each have a conductor distribution which varies sinusoidally with the angular orientation around the drive coils. The conductor distributions in the two sinusoidal coils 32a and 32b are angularly displaced such that the phase of the conductor distribution in coil 32a differs from that in coil 32b. The sinusoidal drive coil as used in the preferred embodiment of this invention has a phase displacement equal to 90° so that coil 32a may be referred to as a sine coil and coil 32b may be referred to as a cosine coil. The space or angular displacement of the conductor distribution between the two phase windings and the time displacement of the current are such that a rotating field of constant angular speed and constant amplitude is generated. FIGS. 9-11 illustrate the rotation of the constant AC magnetic field $B_2$ in the presence of the constant DC magnetic field $B_1$ as the AC magnetic field rotates around the tubing section T containing an axial defect $D_2$.

Velocity and Position Detector

The cross-sectional area of a moving tubular element, the depth of local defects, such as corrosion pitting defects, and the size of longitudinally extending defects, such as defects due to sucker rod interference, can be determined by detector 4 independent of the velocity of the tubular element T relative to the detector. There may also be a need to determine the velocity of the tubular element T relative to the tubing trip tool 2. For example, it may be necessary to not only determine the existence and size of a defect in a particular tubing section of tubular string T, but it may be necessary to determine the position of the defect in both the tubing string and in the constituent tubular section. A noncontact velocity detector 20 is shown positioned on the tubing trip tool head 4 in FIG. 2. The preferred embodiment of each velocity detector used in this invention comprises two detector elements 24a and 24b in which a signal is produced by the magnetic field. In the preferred embodiment of this invention, detector elements 24a and 24b comprise elements in which the voltage is generated due to the Hall effect. These Hall probes 24a and 24b are then incorporated into a velocity detector coil 22 as shown schematically in FIG. 2. The signal produced in the coil is related to both the velocity and the magnetic field sensed by the coil. The signal in the coil is proportional to the vector cross product of the velocity and the magnetic field whereas the signals in the Hall probes are due solely to the magnetic field. The output voltage of a pickup coil near a changing magnetic field is proportional to the rate of change of the field of fixed spatial orientation passing by the coil, then any output voltage is proportional to the product of the field strength and the field velocity.

The changing magnetic fields due to the velocity of the tubular element T are the magnetic leakage fields emanating from the pipe either as pitting signals, as signals due to average wall changes, or as pipe noise. For example, a leakage field is created by permeability fluctuations within the ferromagnetic tubular element T. In the preferred embodiment of each velocity detector, the two Hall probes 24a and 24b are incorporated into the coil 22 with the Hall probes oriented to detect radial changes in the leakage fields. When the coil and Hall probes are oriented as shown in FIG. 2, the coil voltage is equal to the product of the number of turns in the coil, the velocity of the tubular element, the width of the coil, and the difference between the radial components of the magnetic leakage field at the two ends of the coil. The voltage of each Hall probe is equal to the gain of the Hall probe device times the radial component of the leakage field of the Hall probe. The ratio of the coil voltage to the difference in the voltage between the two Hall probes thus determines the pipe velocity.

The velocity detector employed in the tubing trip tool head 4 is located on the exterior of the detector coils 10. The velocity detector can be spaced from the surface of the ferromagnetic tubular element T and need not be in contact with the tubular element. The detector is insensitive to radial position, applied field, signal amplitude and pipe grade. This noncontact velocity measurement is especially useful in conjunction with removal or insertion of the tubing string T from an oil or gas well. In the preferred embodiment of this invention, this velocity measurement permits the operator to determine the axial position along the tubular element and along each individual tubing section.

End Coupling Detector

The noncontact velocity detector described herein can be used to determine the axial position of a defect in an inspected tubular member. Knowledge of the defect location in specific tubular sections forming the tubing string is important, and knowledge of the defect location in the tubing string is also significant in that such knowledge would permit the operator to determine the exact location in the well at which wall thickness reduction, corrosion pitting or wear due to sucker rod interference is a problem. Such knowledge would permit construction of a string profile to determine significant problem areas.

In order to construct a string profile and to accurately obtain information as to the location of defects in any particular tubular string, the position of the tubing string relative to the well head must be determined. In the preferred embodiment of this invention, the location of the tubing string is determined by use of the noncontact velocity detector and by use of a noncontact end coupling detector. For conventional tubular strings, such as casing, production tubing and completion strings used in oil and gas wells, the individual sections are joined by end couplings.

There are two common types of end couplings. The first consists of a collar having internal threads on both ends which is used to join two lengths of casing, tubing or conduit. The cross-sectional area of the separate coupling member and the end portions of the tubing sections engaging the separate member will be greater than the cross-sectional area of the tubular section intermediate its ends. A second type of end coupling comprises an upset section on the ends of adjacent tubing sections. The ends of adjacent tubing sections have mating threads in the vicinity of the upset ends, and the tubular sections are joined directly without the necessity of employing a separate coupling section or collar. These directly engageable tubular sections are, however, upset, with the portion of the tubing section in which threads are machined being thicker than the remaining portion of the tubing section. Thus the cross-sectional area in the vicinity of the end coupling is greater than the cross-sectional area of the tubing intermediate its ends whether a separate collar is used or whether interengageable mating threads are employed on adjacent tubular sections.

Figure 13:
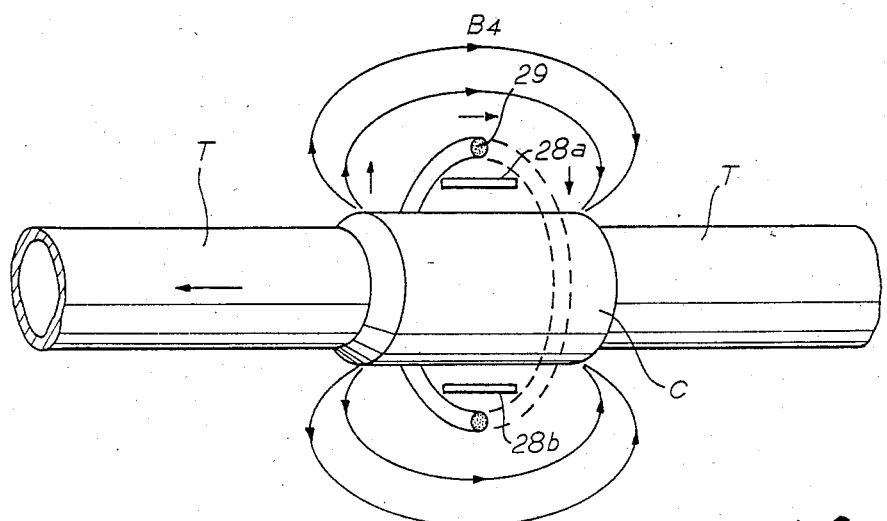
FIG. 13 is a schematic of the end coupling detector employed in the preferred embodiment of this invention.

The exact location of each tubing section, and thus the location within the tubular string can be determined by detecting both the presence and the direction of movement of each end coupling. In the preferred embodiment of this invention, a magnetic field having a uniform strength and fixed relative to the well head is applied to the portion of the tubular string and tubular sections in the vicinity of the well head. An induced magnetic field in the tubular section results. FIG. 13 shows tubing sections T interconnected by end coupling C and the lines of magnetic flux representing the induced magnetic field $B_4$ in the area of end coupling C. Since the cross-sectional area at end coupling C is greater than the cross-sectional area of tubing T, the strength of the magnetic field $B_4$ in the vicinity of the end coupling will be greater than the strength of the magnetic field induced in the tubular section intermediate its ends. If the strength of the magnetic field $B_4$ detected at the well head is greater than a predetermined reference value in excess of the field strength normally induced in a tubing section having a constant cross-sectional area intermediate its ends, the presence of a coupling can be distinguished from normal variations in the strength of the induced magnetic field in the tubing section. In the preferred embodiment of this invention, the strength of the reference signal or the threshold value of the magnitude of the induced magnetic field would be less than the magnitude of the magnetic field normally induced by an end coupling of known dimensions to account for slight variations of the magnetic field included in the coupling.

In normal drilling, production and completion operations, the tubular sections comprising the tubular string are intermittently lowered and raised during either insertion or removal into or from the well. Therefore, simple detection of the presence of an end coupling in the vicinity of the well head will not be sufficient to identify specific tubular sections comprising the tubular string or to identify the location of a tubular section within the tubular string. Therefore, it will be necessary to identify the direction in which the coupling moves with relation to the well head. By identifying both the presence of the coupling at the well head and the direction of movement of the coupling with respect to the well head, each instance in which the coupling passes the well head in either direction can be stored in a conventional memory, and conventional computing means can be provided to tabulate the number and location of each end coupling encountered during insertion or removal of the tubular string into or from the well.

In the preferred embodiment of this invention, each end coupling, and its direction of movement are detected and counted by first magnetically detecting the presence of an end coupling having an enlarged cross-sectional area in the manner previously described. One or more detectors capable of generating signals of opposite signs corresponding to movement of the tubular strings T and end coupling C in opposite directions relative to the detector are employed to determine the direction of movement of an end coupling C. In the preferred embodiment of this invention, an encircling coil 29 similar to encircling pickup coil 30, which is used to determine the average wall thickness of the tubular section, is employed to detect an end coupling C having a greater thickness than the tubular section. Encircling coil 29 functions in the same manner as coil 30 as previously described with respect to measurement of the wall thickness. Indeed an apparatus in accordance with this invention could employ the same encircling coil, both for the wall thickness measurement of the tubular string T and to detect the presence of an enlarged end coupling C.

Once the presence of the end coupling has been detected by encircling coil 29, the direction of movement can be detected by separate detectors, such as detectors 28a and 28b. In the preferred embodiment of this invention, detectors 28a and 28b comprise Hall probes which generate a voltage proportional to the product of the input current, the magnetic flux density, and the sine of the angle between the magnetic flux density and the plane of the Hall generator. These elements are similar to the elements used for corrosion pitting detection and the voltage is produced in response to the electromagnetic phenomenon generally referred to as the Hall effect. The sign of the output voltage of Hall probes 28a and 28b will be opposite when subjected to magnetic lines of force in a magnetic field extending in opposite directions. As shown in FIG. 13, in which the direction of movement of the tubular string T is in the direction of the arrow, the magnetic lines of force of magnetic field $B_4$ extend in the directions shown. Magnetic lines of force for the end coupling C increase in intensity as the end coupling C moves into an applied magnetic field when the magnetic lines of force extend outward as shown. At the trailing edge of the end coupling C, the magnetic lines of force in the induced magnetic field $B_4$ extend inwardly toward the tubular string T and end coupling C as shown schematically in FIG. 13. Thus the Hall probes 28a and 28b will be subjected to magnetic lines of force or flux extending in opposite directions during passage of end coupling C through the applied magnetic field. When the Hall probes 28a and 28b are positioned near the leading edge of the moving end coupling C, the magnetic lines of force will extend radially outward. When the Hall probes 28a and 28b are adjacent the trailing edge of the end coupling C, they will be subjected to magnetic line of forces extending inwardly toward end coupling C. Thus the voltage generated by Hall probes 28a and 28b in the vicinity of the leading edge of end coupling C will have the opposite sign from the voltage generated when the Hall probes 28a and 28b are in the vicinity of the trailing edge of end coupling C. One sequence of the signs of the voltage generated by Hall probes 28a and 28b will correspond to movement of the tubing string T and end coupling C in the direction shown in FIG. 13. Movement of the tubing string T and the end coupling C in the opposite direction will result in an opposite sequence for the signs of the voltage generated by the Hall probes 28a and 28b. Thus the direction of movement of end coupling C through the applied magnetic field can be recognized by conventional computing means and specific tubular sections can be located.

When used in conjunction with a position indicator, such as would be provided by a device capable of measuring the velocity of the tubing string T, a profile of defects, including average wall thickness reduction, corrosion pitting, and wear due to sucker rod interference, can be tabulated as a function of the position of the tubular string in the well. Such information can give the operator valuable insights on the phenomenon being encountered within a subterranean oil or gas well. Furthermore, the use of the end coupling detector and the velocity detector described in the preferred embodiment of this invention will permit an accurate tabulation of defects in individual used tubing sections, to permit the operator to determine if such tubing sections should be replaced.

Although the invention has been described in terms of the specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. An expandable tubular trip tool for use on a surface rig in measuring defects in tubular sections interconnected by end couplings to form continuous tubular string as the tubular sections travel relative to the wellhead of a subterranean well, comprising:

a detection head comprising a plurality of arcuate segments and including means for monitoring the condition of each tubular section, each segment being transversely shiftable from a first position adjacent to the exterior of the tubular sections to a second retracted position spaced outwardly from the first position;

means for mounting the tubular trip tool at the wellhead with the detection head segments surrounding the tubular sections;

means for biasing the detection head segments toward the second position;

means for detecting movement of a component traveling with the tubular section toward the detection head and having an exterior surface radially outwardly from an end coupling traveling through the detection head; and means for expanding the detection head segments upon detection of the component having the exterior surface radially outwardly from the end coupling and for retaining the detection head in the first position when the end couplings move through the detection head.

2. The tubular trip tool of claim 1, wherein the means for detecting movement of the component comprises radially shiftable members axially adjacent and radially movable relative to the detection head segments, the radailly shiftable members having means for engaging protrusions in the tubing string and for radially shifting the detection head segments to provide radial clearance for protrusions having the exterior surface radially outwardly from the end coupling.

3. The tubular trip tool of claim 1, further comprising:
centering means in contact with the surface of the tubular sections for effecting radial displacement of the detection head segments to maintain the tubular sections centered with respect to the detector head segments; and
the detector head segments are transversely spaced from the surface of the tubular sections while in the first position when the centering means is in contact with the surface of the tubing sections.

4. An expandable tubular trip tool for use on a surface rig in measuring defects in tubular sections forming a continuous tubular string as the tubular sections travel relative to the wellhead of a subterranean well, comprising:
a detection head comprising a plurality of arcuate segments and including means for monitoring the characteristics of magnet fields in the tubular sections, each segment being transversely shiftable from a first position adjacent to the exterior of the tubular sections of a second retracted position spaced outwardly from the first position;
means for mounting the tubular trip tool at the wellhead with the detection head segments surrounding the tubular sections;
means for biasing the detection head segments toward the second positions;
means for detecting movement of a component traveling with the tubular section toward the detection head and having an exterior surface radially outwardly from an end coupling traveling through the detection head;
an inflatable toroid surrounding the acruate detection head segments, inflation of the toroid moving the arcuate detection head segments toward the tubular sections;
valve means responsive to the means for detecting movement for deflating the toroid to allow expansion of the deflection head segments; and magnetic field generating means surrounding the detection head, the detection head segments being radially shiftable relative to the magnetic field generating means.

5. The tubular trip tool of claim 4 wherein the means for detecting movement of the component comprises radially shiftable members axially adjacent and radially movable relative to the detection head segments, the radially shiftable members having means for engaging protrusions in the tubular string and for radially shifting the detection head segments to provide radial clearance for protrusions having the exterior surface radially outwardly from the end coupling.

6. The tubular trip tool of claim 5 further comprising a second inflatable toroid surrounding the axially adjacent radially shiftable members, inflation of the second toroid moving the radially shiftable members toward the tubular sections.

7. The tubular trip tool of claim 5 further comprising a plurality of cages, the detection head segments each being positioned within a respective cage, the cage being free to move radially while the detection head segments remain in the first position in response to radial movement of the radial shiftable members upon engagement with tubular sections due to variations of the axial position of the tubular sections relative to the tubular trip tool.

8. The tubular trip tool of claim 4 further comprising centering means in contact with the surface of the tubular sections for effecting radial displacement of the detecting head segments to maintain the tubular sections centered with respect to the detector head segments.

9. The tubular trip tool of claim 8 wherein the detection head segments are transversely spaced from the surface of the tubular sections in the adjacent first position when the centering means is in contact with the surface of the tubing sections.

10. The tubular trip tool of claim 8 further comprising a plurality of cages, the detection head segments each being positioned within a respective cage, the cage being radially displacable when the centering means is rapidly shiftable relative to the tubular trip tool in response to radial movement of the tubular sections relative to the trip tool during axial movement of tubular sections through detector head.

11. An expandable tubular trip tool for use at the wellhead on a surface rig in measuring defects in tubing sections forming a continuous tubular string, during travel of the tubular sections relative to the wellhead of a subterranean well, comprising:
a detection head comprising a plurality of arcuate segments surrounding an axially extending central opening adapted to receive the axially moving tubular sections, the detection head including a first driving coil encircling the central opening, portions of the first driving coil being mounted on each arcuate segment, a first detecting coil within the first driving coil, a second detecting coil encircling the central opening, each arcuate segment being transversely shiftable from an inner position to an outer retracted position;
means for shifting the arcuate segments between the inner and retracted positions; and
a second driving coil encircling the detection head, whereby electric current in the driving coils induce magnetic fields in the tubular sections during axial movement thereof and the response of the detecting coils to the induced magnetic field measure defects within the tubing sections.

12. The expandable tubular trip tool of claim 11 wherein the first driving coil each and the first detecting coil have axially extending portions spaced around the detection head.

13. The expandable tubular trip tool of claim 12 wherein the second dectecting coil extends transversely relative to the axially extending portions of the first detecting coil.

14. The expandable tubular trip tool of claim 13 wherein the second driving coil extends transversely relative to the axially extending portions of the first detecting coil.

15. The expandable tubular trip tool of claim 13 further comprising an obstruction detecting element axially spaced below the detecting head comprising means for sensing the presence of an obstruction on the tubing string to prevent contact with the detection head segments.

16. The expandable tubular trip tool of claim 13 wherein the means for shifting the arcuate segments between the inner and retracted positions comprise inflatable means and opposed biasing means.

17. The expandable tubular trip tool of claim 13 wherein the first and second detecting coils are spaced from the tubing sections when the arcuate segments are in the inner position.

18. The expandable tubular trip tool of claim 13 further comprising a plurality of axially spaced discrete detecting elements, disposed at a plurality of circumferential locations within the first driving coil.

19. The expandable tubular trip tool of claim 11 wherein the first driving coil and the first detecting coil each comprise a pair of conductor cils, each conductor coil being activated by a sinusoidal power input distribution around the central opening, the sinusoidal distribution of one of the conductor coils of the first driving coil and the first detecting coil being offset from the distribution of the other conductor coils of the first driving coil and the first detecting coil.

20. The expandable tubular trip tool of claim 19 wherein the sinusoidal power input distribution of one of the conductor coils is offset by 90° with respect to the sinusoidal power input distribution of the other coil at the conductor coils.

21. A method for use on a surface rig in measuring defects in tubular sections forming a continuous tubular string at the wellhead, as the tubular sections travel relative to the wellhead of a subterranean well, comprising the steps of:

disposing a detection head containing a plurality of arcuately segmented detector elements for monitoring the characteristics of magnetic fields induced in the tubular sections, around the tubular string of the wellhead, each segment being transversely shiftable from a first position adjacent to the exterior of the tubular sections to a second retracted position spaced outwardly from the first position;

biasing the detector elements toward the second position;

detecting movement of a component traveling with the tubular section toward the detection head and having an exterior surface radially outwardly from an end coupling traveling through the detection head; and expanding the detection head segments upon detection of the component having the exterior surface radially outwardly from the end coupling and for retaining the detection head in the first position when the end couplings move through the detection head.

22. The method of claim 21 further comprising:

disposing an inflatable toroidal member surrounding the detection head segments;

inflating the toroidal member to move the detector elements toward the tubular sections; and deflating the toroidal member to allow expansion of the detection head segments upon detection of the component.

23. The method of claim 21 wherein detecting movement of the component comprises:

disposing radially shiftable members axially adjacent and radially movable relative to the detection head segments for engagement with the exterior surface radially outwardly from the end coupling for expanding the detection head segments.

24. The method of claim 21 further comprising:

disposing centering means in contact with the surface of the tubular sections for effecting radial displacement of the detecting head segments to maintain the tubular sections centered with respect to detector head segments; and disposing the detection head segments transversely spaced from the surface of the tubular sections while in the first position when the centering means is in contact with the surface of the tubing sections.

* * * * *